(12) United States Patent
Blumenstyk (10) Patent No.: US 11,147,562 B2
(45) Date of Patent: Oct. 19, 2021

(54) SYSTEMS AND METHODS FOR EMBOLIC IMPLANT DETACHMENT

(71) Applicant: DePuy Synthes Products, Inc., Raynham, MA (US)

(72) Inventor: David Blumenstyk, Raynham, MA (US)

(73) Assignee: DEPUY SYNTHES PRODUCTS, INC., Raynham, MA (US)

( * ) Notice: Subject to any disclaimer, the term of this patent is extended or adjusted under 35 U.S.C. 154(b) by 109 days.

(21) Appl. No.: 16/218,342

(22) Filed: Dec. 12, 2018

(65) Prior Publication Data
US 2020/0187951 A1    Jun. 18, 2020

(51) Int. Cl.
*A61B 17/12* (2006.01)
*A61F 2/01* (2006.01)
*A61F 2/95* (2013.01)

(52) U.S. Cl.
CPC .... *A61B 17/12113* (2013.01); *A61B 17/1214* (2013.01); *A61F 2/01* (2013.01); *A61F 2/95* (2013.01); *A61B 2017/12054* (2013.01); *A61F 2/011* (2020.05)

(58) Field of Classification Search
None
See application file for complete search history.

(56) References Cited

U.S. PATENT DOCUMENTS

| 3,429,408 A | 2/1969 | Maker et al. |
|---|---|---|
| 5,108,407 A | 4/1992 | Geremia et al. |
| 5,122,136 A | 6/1992 | Guglielmi et al. |
| 5,250,071 A | 10/1993 | Palermo |
| 5,263,964 A | 11/1993 | Purdy |

(Continued)

FOREIGN PATENT DOCUMENTS

| EP | 1985244 A2 | 10/2008 |
|---|---|---|
| EP | 2498691 | 9/2012 |

(Continued)

OTHER PUBLICATIONS

Extended European Search Report issued in corresponding European Patent Application No. 19 21 5318 dated Apr. 8, 2020.

(Continued)

*Primary Examiner* — Shaun L David
(74) *Attorney, Agent, or Firm* — Troutman Pepper Hamilton Sanders LLP (57) ABSTRACT

An aneurysm treatment system that includes an embolic implant, a delivery system, and an introducer sheath that are collectively designed so that the combination of the introducer sheath and the delivery system can be used as a deployment apparatus for the embolic implant. The delivery system can have a pull wire, a delivery tube, and an interference feature attached to the pull wire and positioned near a proximal end of the delivery tube. Rather than being discarded, the introducer sheath can be moved proximally over the delivery tube until it engages the interference feature. To deploy the implant, the introducer sheath can be pressed against the interference feature, causing the interference feature to move proximally in relation to the delivery tube, thereby proximally pulling the pull wire to which the interference feature is attached and deploying the implant.

20 Claims, 6 Drawing Sheets

(56) References Cited

U.S. PATENT DOCUMENTS

| | | |
|---|---|---|
| 5,334,210 A | 8/1994 | Gianturco |
| 5,350,397 A | 9/1994 | Palermo et al. |
| 5,382,259 A | 1/1995 | Phelps et al. |
| 5,484,409 A | 1/1996 | Atkinson et al. |
| 5,569,221 A | 10/1996 | Houser et al. |
| 5,899,935 A | 5/1999 | Ding |
| 5,925,059 A | 7/1999 | Palermo et al. |
| 6,113,622 A | 9/2000 | Hieshima |
| 6,203,547 B1 | 3/2001 | Nguyen et al. |
| 6,391,037 B1 | 5/2002 | Greenhalgh |
| 6,454,780 B1 | 9/2002 | Wallace |
| 6,506,204 B2 | 1/2003 | Mazzocchi |
| 6,561,988 B1 | 5/2003 | Turturro et al. |
| 7,367,987 B2 | 5/2008 | Balgobin et al. |
| 7,371,251 B2 | 5/2008 | Mitelberg et al. |
| 7,371,252 B2 | 5/2008 | Balgobin et al. |
| 7,377,932 B2 | 5/2008 | Mitelberg et al. |
| 7,708,754 B2 | 5/2010 | Balgobin et al. |
| 7,708,755 B2 | 5/2010 | Davis, III et al. |
| 7,799,052 B2 | 9/2010 | Balgobin et al. |
| 7,811,305 B2 | 10/2010 | Balgobin et al. |
| 7,819,891 B2 | 10/2010 | Balgobin et al. |
| 7,819,892 B2 | 10/2010 | Balgobin et al. |
| 7,901,444 B2 | 3/2011 | Slazas |
| 7,985,238 B2 | 7/2011 | Balgobin et al. |
| 8,062,325 B2 | 11/2011 | Mitelberg et al. |
| 8,333,796 B2 | 12/2012 | Tompkins et al. |
| 9,155,540 B2 | 10/2015 | Lorenzo |
| 9,232,992 B2 | 1/2016 | Heidner et al. |
| 9,314,326 B2 | 4/2016 | Wallace et al. |
| 9,532,792 B2 | 1/2017 | Galdonik et al. |
| 9,532,873 B2 | 1/2017 | Kelley |
| 9,533,344 B2 | 1/2017 | Monetti et al. |
| 9,539,011 B2 | 1/2017 | Chen et al. |
| 9,539,022 B2 | 1/2017 | Bowman |
| 9,539,122 B2 | 1/2017 | Burke et al. |
| 9,539,382 B2 | 1/2017 | Nelson |
| 9,549,830 B2 | 1/2017 | Bruszewski et al. |
| 9,554,805 B2 | 1/2017 | Tompkins et al. |
| 9,561,125 B2 | 2/2017 | Bowman et al. |
| 9,572,982 B2 | 2/2017 | Burnes et al. |
| 9,579,484 B2 | 2/2017 | Barnell |
| 9,585,642 B2 | 3/2017 | Dinsmoor et al. |
| 9,615,832 B2 | 4/2017 | Bose et al. |
| 9,615,951 B2 | 4/2017 | Bennett et al. |
| 9,622,753 B2 | 4/2017 | Cox |
| 9,636,115 B2 | 5/2017 | Henry et al. |
| 9,636,439 B2 | 5/2017 | Chu et al. |
| 9,642,675 B2 | 5/2017 | Werneth et al. |
| 9,655,633 B2 | 5/2017 | Leynov et al. |
| 9,655,645 B2 | 5/2017 | Staunton |
| 9,655,989 B2 | 5/2017 | Cruise et al. |
| 9,662,120 B2 | 5/2017 | Lagodzki et al. |
| 9,662,129 B2 | 5/2017 | Galdonik et al. |
| 9,662,238 B2 | 5/2017 | Dwork et al. |
| 9,662,425 B2 | 5/2017 | Lilja et al. |
| 9,668,898 B2 | 6/2017 | Wong |
| 9,675,477 B2 | 6/2017 | Thompson |
| 9,675,782 B2 | 6/2017 | Connolly |
| 9,676,022 B2 | 6/2017 | Ensign |
| 9,692,557 B2 | 6/2017 | Murphy |
| 9,693,852 B2 | 7/2017 | Lam et al. |
| 9,700,262 B2 | 7/2017 | Janik et al. |
| 9,700,399 B2 | 7/2017 | Acosta-Acevedo |
| 9,717,421 B2 | 8/2017 | Griswold et al. |
| 9,717,500 B2 | 8/2017 | Tieu et al. |
| 9,717,502 B2 | 8/2017 | Teoh et al. |
| 9,724,103 B2 | 8/2017 | Cruise et al. |
| 9,724,526 B2 | 8/2017 | Strother et al. |
| 9,750,565 B2 | 9/2017 | Bloom et al. |
| 9,757,260 B2 | 9/2017 | Greenan |
| 9,764,111 B2 | 9/2017 | Gulachenski |
| 9,770,251 B2 | 9/2017 | Bowman |
| 9,770,577 B2 | 9/2017 | Li |
| 9,775,621 B2 | 10/2017 | Tompkins et al. |
| 9,775,706 B2 | 10/2017 | Paterson |
| 9,775,732 B2 | 10/2017 | Khenansho |
| 9,788,800 B2 | 10/2017 | Mayoras, Jr. |
| 9,795,391 B2 | 10/2017 | Saatchi et al. |
| 9,801,980 B2 | 10/2017 | Karino et al. |
| 9,808,599 B2 | 11/2017 | Bowman |
| 9,833,252 B2 | 12/2017 | Sepetka |
| 9,833,604 B2 | 12/2017 | Lam |
| 9,833,625 B2 | 12/2017 | Waldhauser et al. |
| 9,918,718 B2 | 3/2018 | Lorenzo |
| 10,285,710 B2 | 5/2019 | Lorenzo et al. |
| 10,517,604 B2 | 12/2019 | Bowman et al. |
| 10,806,402 B2 | 10/2020 | Cadieu et al. |
| 10,806,461 B2 | 10/2020 | Lorenzo |
| 2001/0049519 A1 | 12/2001 | Holman et al. |
| 2002/0072705 A1 | 6/2002 | Vrba et al. |
| 2002/0165569 A1 | 11/2002 | Ramzipoor et al. |
| 2004/0034363 A1 | 2/2004 | Wilson et al. |
| 2004/0059367 A1* | 3/2004 | Davis ............... A61B 17/12022 606/191 |
| 2004/0087964 A1* | 5/2004 | Diaz ................. A61B 17/1214 606/108 |
| 2006/0025801 A1 | 2/2006 | Lulo et al. |
| 2006/0064151 A1 | 3/2006 | Guterman et al. |
| 2006/0116711 A1 | 6/2006 | Elliott et al. |
| 2006/0116714 A1 | 6/2006 | Sepetka et al. |
| 2006/0135986 A1 | 6/2006 | Wallace et al. |
| 2006/0206139 A1 | 9/2006 | Tekulve |
| 2006/0247677 A1 | 11/2006 | Cheng et al. |
| 2006/0276824 A1 | 12/2006 | Mitelberg et al. |
| 2006/0276825 A1 | 12/2006 | Mitelberg et al. |
| 2006/0276826 A1 | 12/2006 | Mitelberg et al. |
| 2006/0276827 A1 | 12/2006 | Mitelberg et al. |
| 2006/0276830 A1 | 12/2006 | Balgobin et al. |
| 2006/0276833 A1 | 12/2006 | Balgobin et al. |
| 2007/0010850 A1* | 1/2007 | Balgobin ......... A61B 17/12113 606/200 |
| 2007/0055302 A1 | 3/2007 | Henry et al. |
| 2007/0083132 A1 | 4/2007 | Sharrow |
| 2007/0233168 A1 | 10/2007 | Davis et al. |
| 2007/0270903 A1 | 11/2007 | Davis, III et al. |
| 2008/0027561 A1 | 1/2008 | Mitelberg et al. |
| 2008/0045997 A1 | 2/2008 | Balgobin et al. |
| 2008/0097462 A1 | 4/2008 | Mitelberg et al. |
| 2008/0281350 A1 | 11/2008 | Sepetka et al. |
| 2008/0300616 A1 | 12/2008 | Que et al. |
| 2008/0306503 A1 | 12/2008 | Que et al. |
| 2009/0062726 A1 | 3/2009 | Ford et al. |
| 2009/0312748 A1 | 12/2009 | Johnson et al. |
| 2010/0114017 A1 | 5/2010 | Lenker et al. |
| 2010/0324649 A1 | 12/2010 | Mattsson et al. |
| 2011/0202085 A1 | 8/2011 | Loganathan et al. |
| 2011/0295303 A1 | 12/2011 | Freudenthal |
| 2012/0035707 A1 | 2/2012 | Mitelberg et al. |
| 2012/0041472 A1 | 2/2012 | Tan et al. |
| 2012/0283768 A1 | 11/2012 | Cox et al. |
| 2013/0066413 A1* | 3/2013 | Jin ........................ A61F 2/966 623/1.12 |
| 2014/0058435 A1 | 2/2014 | Jones et al. |
| 2014/0135812 A1 | 5/2014 | Divino et al. |
| 2014/0200607 A1 | 7/2014 | Sepetka et al. |
| 2014/0277084 A1 | 9/2014 | Mirigian et al. |
| 2014/0277085 A1 | 9/2014 | Mirigian et al. |
| 2014/0277092 A1 | 9/2014 | Teoh et al. |
| 2014/0277093 A1* | 9/2014 | Guo ................. A61B 17/12022 606/200 |
| 2015/0005808 A1 | 1/2015 | Chouinard et al. |
| 2015/0182227 A1* | 7/2015 | Le .................... A61B 17/12154 606/200 |
| 2015/0230802 A1 | 8/2015 | Lagodzki et al. |
| 2015/0335333 A1 | 11/2015 | Jones et al. |
| 2016/0008003 A1 | 1/2016 | Kleshinski et al. |
| 2016/0022275 A1 | 1/2016 | Garza |
| 2016/0157869 A1 | 6/2016 | Elgård et al. |
| 2016/0228125 A1* | 8/2016 | Pederson, Jr. ...... A61B 17/1214 |
| 2016/0310304 A1* | 10/2016 | Mialhe ............. A61B 17/12172 |
| 2016/0346508 A1 | 12/2016 | Williams et al. |
| 2017/0007264 A1 | 1/2017 | Cruise et al. |
| 2017/0007265 A1 | 1/2017 | Guo et al. |

(56) References Cited

U.S. PATENT DOCUMENTS

| | | |
|---|---|---|
| 2017/0020670 A1 | 1/2017 | Murray et al. |
| 2017/0020700 A1 | 1/2017 | Bienvenu |
| 2017/0027640 A1 | 2/2017 | Kunis et al. |
| 2017/0027692 A1 | 2/2017 | Bonhoeffer |
| 2017/0027725 A1 | 2/2017 | Argentine |
| 2017/0035436 A1 | 2/2017 | Morita |
| 2017/0035567 A1 | 2/2017 | Duffy |
| 2017/0042548 A1 | 2/2017 | Lam |
| 2017/0049596 A1 | 2/2017 | Schabert |
| 2017/0071737 A1 | 3/2017 | Kelley |
| 2017/0072452 A1 | 3/2017 | Monetti et al. |
| 2017/0079671 A1 | 3/2017 | Morero |
| 2017/0079680 A1 | 3/2017 | Bowman |
| 2017/0079766 A1 | 3/2017 | Wang |
| 2017/0079767 A1 | 3/2017 | Leon-Yip |
| 2017/0079812 A1 | 3/2017 | Lam et al. |
| 2017/0079817 A1 | 3/2017 | Sepetka |
| 2017/0079819 A1 | 3/2017 | Pung et al. |
| 2017/0079820 A1 | 3/2017 | Lam et al. |
| 2017/0086851 A1 | 3/2017 | Wallace |
| 2017/0086996 A1 | 3/2017 | Peterson et al. |
| 2017/0095258 A1 | 4/2017 | Tassoni et al. |
| 2017/0095259 A1 | 4/2017 | Tompkins et al. |
| 2017/0100126 A1 | 4/2017 | Bowman et al. |
| 2017/0100141 A1 | 4/2017 | Morero et al. |
| 2017/0100143 A1 | 4/2017 | Granfield |
| 2017/0100183 A1 | 4/2017 | Iaizzo |
| 2017/0113023 A1 | 4/2017 | Steingisser et al. |
| 2017/0147765 A1 | 5/2017 | Mehta |
| 2017/0151032 A1 | 6/2017 | Loisel |
| 2017/0165062 A1 | 6/2017 | Rothstein |
| 2017/0165065 A1 | 6/2017 | Rothstein |
| 2017/0165454 A1 | 6/2017 | Tuohy |
| 2017/0172581 A1 | 6/2017 | Bose et al. |
| 2017/0172766 A1 | 6/2017 | Vong et al. |
| 2017/0172772 A1 | 6/2017 | Khenansho |
| 2017/0189033 A1 | 7/2017 | Sepetka et al. |
| 2017/0189035 A1 | 7/2017 | Porter |
| 2017/0215902 A1 | 8/2017 | Leynov et al. |
| 2017/0216484 A1 | 8/2017 | Cruise et al. |
| 2017/0224350 A1 | 8/2017 | Shimizu et al. |
| 2017/0224355 A1 | 8/2017 | Bowman et al. |
| 2017/0224467 A1 | 8/2017 | Piccagli et al. |
| 2017/0224511 A1 | 8/2017 | Dwork et al. |
| 2017/0224953 A1 | 8/2017 | Tran et al. |
| 2017/0231749 A1 | 8/2017 | Perkins et al. |
| 2017/0245864 A1 | 8/2017 | Franano et al. |
| 2017/0245885 A1 | 8/2017 | Lenker |
| 2017/0252064 A1 | 9/2017 | Staunton |
| 2017/0258476 A1 | 9/2017 | Hayakawa et al. |
| 2017/0265983 A1 | 9/2017 | Lam et al. |
| 2017/0281192 A1 | 10/2017 | Tieu et al. |
| 2017/0281331 A1 | 10/2017 | Perkins et al. |
| 2017/0281344 A1 | 10/2017 | Costello |
| 2017/0281909 A1 | 10/2017 | Northrop et al. |
| 2017/0281912 A1 | 10/2017 | Melder |
| 2017/0290593 A1 | 10/2017 | Cruise et al. |
| 2017/0290654 A1 | 10/2017 | Sethna |
| 2017/0296324 A1 | 10/2017 | Argentine |
| 2017/0296325 A1 | 10/2017 | Marrocco et al. |
| 2017/0303939 A1 | 10/2017 | Greenhalgh |
| 2017/0303942 A1 | 10/2017 | Greenhalgh et al. |
| 2017/0303947 A1 | 10/2017 | Greenhalgh |
| 2017/0303948 A1 | 10/2017 | Wallace et al. |
| 2017/0304041 A1 | 10/2017 | Argentine |
| 2017/0304097 A1 | 10/2017 | Corwin et al. |
| 2017/0304595 A1 | 10/2017 | Nagasrinivasa |
| 2017/0312109 A1 | 11/2017 | Le |
| 2017/0312484 A1 | 11/2017 | Shipley et al. |
| 2017/0316561 A1 | 11/2017 | Helm et al. |
| 2017/0319826 A1 | 11/2017 | Bowman |
| 2017/0333228 A1 | 11/2017 | Orth et al. |
| 2017/0333236 A1 | 11/2017 | Greenan |
| 2017/0333678 A1 | 11/2017 | Bowman |
| 2017/0340383 A1 | 11/2017 | Bloom et al. |
| 2017/0348014 A1 | 12/2017 | Wallace |
| 2017/0348514 A1 | 12/2017 | Guyon et al. |
| 2018/0028779 A1 | 2/2018 | von Oepen et al. |
| 2018/0036508 A1 | 2/2018 | Ozasa et al. |
| 2018/0228493 A1 | 8/2018 | Aguilar et al. |
| 2018/0250150 A1* | 9/2018 | Majercak ........... A61B 17/3468 |
| 2018/0280667 A1 | 10/2018 | Keren |
| 2018/0325706 A1* | 11/2018 | Hebert ............. A61B 17/12031 |
| 2019/0159784 A1 | 5/2019 | Sananes et al. |
| 2019/0192162 A1 | 6/2019 | Lorenzo |
| 2019/0255290 A1 | 8/2019 | Snyder et al. |
| 2019/0314033 A1 | 10/2019 | Mirigian et al. |
| 2019/0328398 A1 | 10/2019 | Lorenzo |
| 2020/0138448 A1 | 5/2020 | Dasnurkar et al. |
| 2020/0187951 A1 | 6/2020 | Blumenstyk |
| 2021/0001082 A1 | 1/2021 | Lorenzo et al. |

FOREIGN PATENT DOCUMENTS

| | | |
|---|---|---|
| EP | 3092956 A1 | 11/2016 |
| EP | 3501427 A1 | 6/2019 |
| JP | 2006-334408 A | 12/2006 |
| JP | 2012-523943 A | 10/2012 |
| JP | 2013-78584 A | 5/2013 |
| WO | WO 2009/132045 A2 | 10/2009 |
| WO | WO 2012/158152 A1 | 11/2012 |
| WO | WO 2017/066386 A1 | 4/2017 |
| WO | WO 2018/022186 A1 | 2/2018 |

OTHER PUBLICATIONS

Extended European Search Report issued in corresponding European Patent Application No. 20 21 2970 dated May 28, 2021.

Extended European Search Report issued in European Patent Application No. 21 15 6857 dated Jun. 22, 2021.

* cited by examiner

SYSTEMS AND METHODS FOR EMBOLIC IMPLANT DETACHMENT

FIELD OF INVENTION

The present invention generally relates to aneurysm treatment devices and more particularly, to delivery systems for embolic implants.

BACKGROUND

Numerous intravascular implant devices are known in the field. Many are deployed mechanically, via systems that combine one or more catheters and wires for delivery. Examples of implants that can be delivered mechanically include embolic elements, stents, grafts, drug delivery implants, flow diverters, filters, stimulation leads, sensing leads, or other implantable structures delivered through a microcatheter. Some obstetric and gastrointestinal implants may also be implanted via similar systems that combine one or more catheters and wires. Devices that may be released or deployed by mechanical means vary greatly in design but can employ a similar delivery catheter and wire system. Many such catheter-based delivery systems include a wire for retention of the implant in the catheter until the time for release of the device. These systems are then actuated by retracting or pulling the wire relative to the catheter. Such a wire is referred to herein as a "pull wire".

To pull the pull wire proximally to deploy the implant, a physician can use one of many known deployment apparatuses. Such mechanical deployment apparatuses are typically separate from the delivery system and have moving parts for gripping the pull wire and for moving the pull wire proximally. Deployment methods and apparatuses that do not require auxiliary components and/or complex moving parts can simplify treatment procedures and reduce cost. There is therefore a need for simplified mechanical implant deployment apparatuses.

SUMMARY

Disclosed herein are various exemplary systems, devices, and methods of the present invention that can address the above needs. Examples can generally include an embolic implantation system that includes an embolic implant, a delivery system, and an introducer sheath that are collectively designed so that the combination of the introducer sheath and the delivery system can be used as a deployment apparatus for the embolic implant. The delivery system can have a pull wire, a delivery tube, and an interference feature attached to the pull wire and positioned at a proximal end of the delivery tube. The introducer sheath can be moved proximally over the delivery tube until it engages the interference feature. To deploy the implant, the introducer sheath can be pressed against the interference feature, causing the interference feature to move proximally in relation to the delivery tube, thereby proximally pulling the pull wire to which the interference feature is attached and deploying the implant.

An example implantation system can include a delivery tube, an embolic coil, an introducer sheath, an interference feature, and an elongated member. The embolic coil can be detachably attached to a distal end of the delivery tube. The interference feature can be positioned at a proximal end of the delivery tube and movable in relation to the delivery tube. The elongated member can be positioned within a lumen of the delivery tube and attached to the interference feature. The introducer sheath can have a lumen sized to slidably receive the delivery tube and the embolic coil, the introducer sheath can be translatable over the delivery tube from the distal end of the delivery tube to the proximal end of the delivery tube, and the introducer sheath can be sized to engage the interference feature. The interference feature can be movable in relation to the delivery tube in response to a force applied by the introducer sheath against the interference feature. The elongated member can be movable in relation to the delivery tube in response to a proximal movement of the interference feature.

The interference feature can be detachable from the delivery tube. The elongated member can be movable to exit the proximal end of the delivery tube in response to a proximal movement of the detached interference feature.

The delivery tube can have a soft section near the distal end of the delivery tube. The length of the embolic coil and the soft section as measured from a distal end of the un-implanted embolic coil to a proximal end of the soft section can be shorter than the end-to-end length of the introducer sheath so that the introducer sheath is sized to fully encompass the un-implanted embolic coil and the soft section. The introducer sheath can be longer than the length of the embolic coil and soft section by about 5 cm.

The system can include a microcatheter, and the delivery tube can have an end-to-end length that is longer than the sum of the end-to-end length of the introducer sheath and an end-to-end length of the microcatheter.

The end-to-end length of the introducer sheath can be between about 46 cm to about 105 cm.

The introducer sheath can be movable from a packaged configuration in which the introducer sheath is positioned to completely encompass the soft section and the embolic coil to a deployment configuration in which the introducer sheath is engaged with the interference feature.

The embolic coil can be detached from the delivery tube by moving the elongated member proximally in relation to the delivery tube.

The interference feature can have a substantially circular surface positioned to engage the proximal end of the introducer sheath.

A distal end of the introducer sheath can be sized to engage a microcatheter to create an enclosed interface through which the embolic coil and at least a portion of the delivery tube can pass.

An example implantation assembly can include a delivery tube, an embolic implant, a pull wire, an engagement bump, and a tubular sheath. The embolic implant can be attached to a distal end of the delivery tube. The pull wire can be disposed within a lumen of the delivery tube and movable to detach the embolic implant from the delivery tube. The engagement bump can be disposed on a proximal end of the pull wire and positioned near a proximal end of the delivery tube. The tubular sheath can be conveyable over the embolic implant and the delivery tube from a distal end of the embolic implant to the proximal end of the delivery tube, and the tubular sheath can be sized to engage the engagement bump. The engagement bump and the pull wire can be movable in relation to the delivery tube in response to a force applied by the tubular sheath to the engagement bump.

The delivery tube can have a soft section extending proximally from the distal end of the delivery tube, and the tubular sheath can measure end-to-end about 5 cm longer than a length measured from a distal end of the embolic implant to a proximal end of the soft section when the embolic implant is attached to the delivery tube and extended in an un-implanted configuration.

The assembly can include a microcatheter, and the delivery tube can have an end-to-end length that is greater than the sum of the length of the introducer sheath and the microcatheter.

The tubular sheath can be movable from a packaged configuration in which the tubular sheath is positioned to completely encompass the soft section and the embolic coil to a deployment configuration in which the tubular sheath is engaged with the engagement bump.

The engagement bump can be detachable from the delivery tube in response to the force applied by the tubular sheath to the engagement bump. The pull wire can be movable to detach the embolic implant from the delivery tube in response to the force applied by the tubular sheath to the engagement bump.

An example method for treating an aneurysm can include the steps of providing an implantation system including an embolic implant, an introducer sheath, a delivery tube, an interference feature, and a pull wire; affixing the pull wire to the interference feature; positioning the pull wire within a lumen of the delivery tube; attaching the interference feature to a proximal end of the delivery tube; attaching the embolic implant at a distal end of the delivery tube; positioning the introducer sheath to encompass the embolic implant and a first portion of the delivery tube; sliding the introducer sheath proximally over the delivery tube; pulling the introducer sheath proximally to apply a force from the introducer sheath to the interference feature; and moving the interference feature and the pull wire proximally in relation to the delivery tube in response to the force.

The first portion of the delivery tube over which the introducer sheath is positioned in the example method can have a soft section. The method can include sizing the introducer sheath to have a length that is greater than the length of the embolic implant and the soft section by about 5 cm. The method can include sizing the introducer sheath to have a length of between about 46 cm to about 105 cm, the length measurable from a distal end to a proximal end of the introducer sheath.

The method can include detaching the embolic implant from the delivery tube in response to moving the interference feature and the pull wire proximally in relation to the delivery tube. The method can include detaching the interference feature from the delivery tube. The interference feature can be detached in response to moving the interference feature and the pull wire proximally in relation to the delivery tube.

The method can include providing a microcatheter; positioning the introducer sheath to engage with the microcatheter while maintaining the embolic implant and the first portion of the delivery tube within the inducer sheath; and translating the embolic implant and the delivery tube distally to position the embolic implant and the first portion of the delivery tube within the microcatheter.

BRIEF DESCRIPTION OF THE DRAWINGS

The above and further aspects of this invention are further discussed with reference to the following description in conjunction with the accompanying drawings, in which like numerals indicate like structural elements and features in various figures. The drawings are not necessarily to scale, emphasis instead being placed upon illustrating principles of the invention. The figures depict one or more implementations of the inventive devices, by way of example only, not by way of limitation.

DETAILED DESCRIPTION

Examples presented herein utilize an introducer sheath to facilitate mechanical deployment of an implant. Examples of implants that can be delivered mechanically include embolic elements, stents, grafts, drug delivery implants, flow diverters, filters, stimulation leads, sensing leads, or other implantable structures deliverable through a microcatheter. Some implants are currently packaged with an introducer sheath that is removed from the device and discarded near the beginning of an implantation procedure. For example, in existing systems, embolic coils and other embolic implants can be used to occlude vessels in a variety of medical applications. In many instances, prior to implantation and during handling of an embolic implant outside of a patient, the embolic implant is contained in an introducer sheath. In present treatment practices, once the embolic implant is transferred to a microcatheter, the introducer sheath would be removed from the delivery system and discarded before the embolic implant reaches a treatment site. In examples presented herein, according to the present invention, rather than being discarded, the introducer sheath can be slid proximally and can facilitate deployment of the embolic implant, i.e. detachment of the embolic implant from the delivery system. In order to use the introducer sheath to facilitate deployment, the delivery system can have an interference feature positioned at a proximal end of a delivery tube and attached to a pull wire, and the combination of the introducer sheath, delivery tube, pull wire, and interference feature can be configured such that the introducer sheath can engage with the interference feature and move the interference feature proximally in relation to the delivery tube, thereby pulling the pull wire proximally and deploying the embolic implant. The delivery tube, microcatheter, and introducer sheath can each have a respective length sized such that the introducer sheath can be long enough to cover the embolic implant and sensitive portions of the delivery system, and the delivery tube can be long enough to extend through the entire length of the microcatheter and the entire length of the introducer sheath.

Figures 1, 2A:
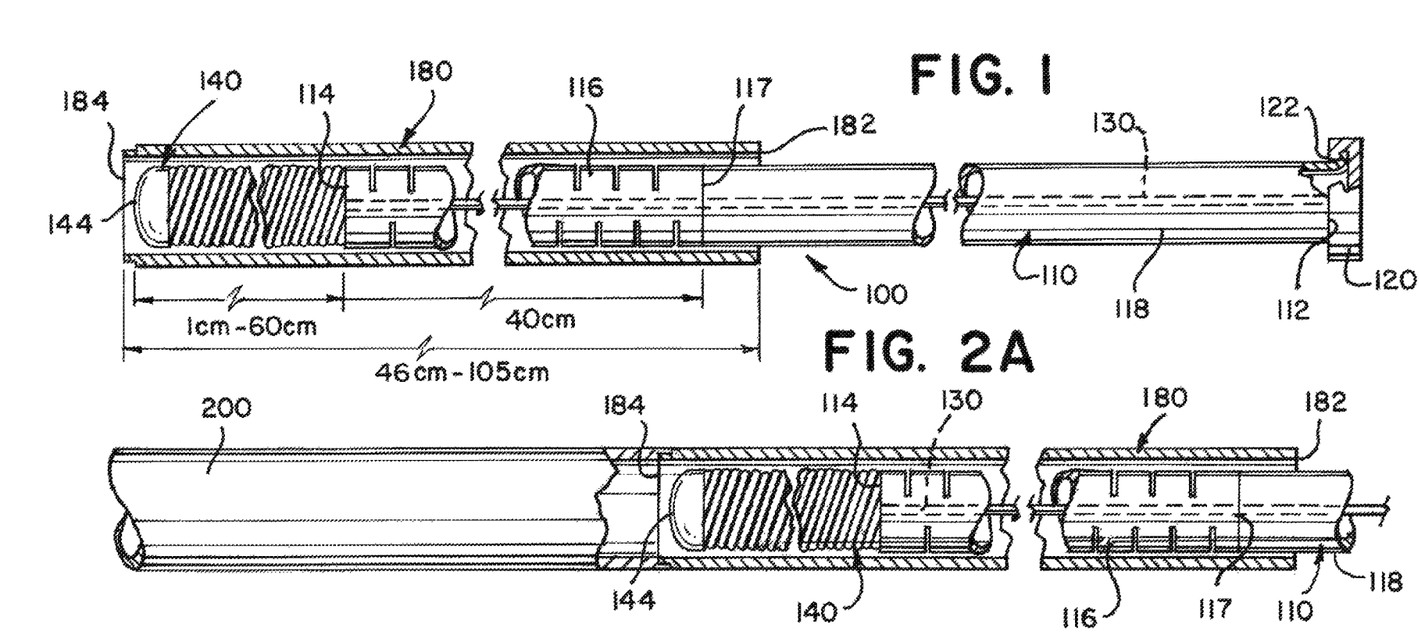
FIG. 1 is an illustration of an exemplary implantation system according to aspects of the present invention.
FIGS. 2A and 2B are illustrations of an exemplary implantation system such as illustrated in FIG. 1 interfacing with a microcatheter according to aspects of the present invention.

FIG. 1 is an illustration of an exemplary implantation system 100. The implantation system 100 can have an embolic implant 140 such as an embolic coil, embolic braid, or other such implant for filling an aneurysm sac, a delivery tube 110 for delivering the embolic implant 140 to a treatment site, a pull wire 130 disposed within the delivery tube that can be pulled proximally to deploy the embolic implant 140, an interference feature 120 positioned at a proximal end 112 of the delivery tube 110 attached to the pull wire 130 that can be pulled proximally to pull the pull wire 130 proximally, and an introducer sheath 180 that can be moved proximally to engage the interference feature 120 and pull the interference feature 120 proximally.

The introducer sheath 180 can have a lumen therethrough that is sized to slidably receive the delivery tube 110 and the embolic implant 140. The introducer sheath 180 can be sized such that it can be translated proximally from the position illustrated in FIG. 1 over a length of the delivery tube 110 to engage the interference feature 120 positioned at the proximal end 112 of the delivery tube 110.

The interference feature 120 can be movable in relation to the delivery tube 110. For example, the interference feature 120 can be detachably attached to the proximal end 112 of the delivery tube 110, and the system 100 can include a disconnection feature 122 that can be unhooked, torn, broken, twisted, or otherwise manipulated to disconnect the interference feature 120 from the delivery tube 110.

The delivery tube 110 can have a soft section 116 positioned near a distal end 114 of the delivery tube 110 that has a greater flexibility than the remainder (proximal portion) 118 of the delivery tube 110. The embolic implant 140 can be detachably attached to a distal end 114 of the delivery tube 114. The soft section 116 can be designed to allow greater control and stability of the distal end 114 of the delivery tube 110 during implantation and deployment of the embolic implant 140. The soft section 116 can have laser cut notches or groves, and/or the soft section 116 can be made of a more flexible material compared to the remainder 118 of the delivery tube 110.

The introducer sheath 180 can serve the purpose of protecting (packaging) the embolic implant 140 and the soft section 116 of the delivery tube 110 as the system 100 is being handled prior to, and at the beginning of a patient treatment procedure. For this purpose, it is therefore desirable for the introducer sheath 180 to be long enough to completely encompass the embolic implant 140 and the soft section 116 prior to the treatment procedure. The combined length of the embolic implant 140 and the soft section 116 can be measured from a distal end 144 of the embolic implant 140 to a proximal end 117 of the soft section 116. The introducer sheath 180 can have a length measurable from a distal end 184 to a proximal end 182 of the introducer sheath that can be sized a few centimeters longer than the combined length of the embolic implant 140 and the soft section 116 to ensure that the embolic implant 140 and soft section 116 remain protected in case portions of the system 100 shift during handling prior to the treatment procedure. The introducer sheath 180 can have a length that is about 5 cm longer than the combined length of the embolic implant 140 and the soft section 116. For example, the embolic implant 140 can have a length of between about 1 cm and about 60 cm, the soft section 116 can have a length of about 40 cm, and the introducer sheath can have a length that is about 5 cm longer than the sum of the embolic implant 140 length and the soft section 116 length, i.e. between about 46 cm and about 105 cm.

Figure 2B:
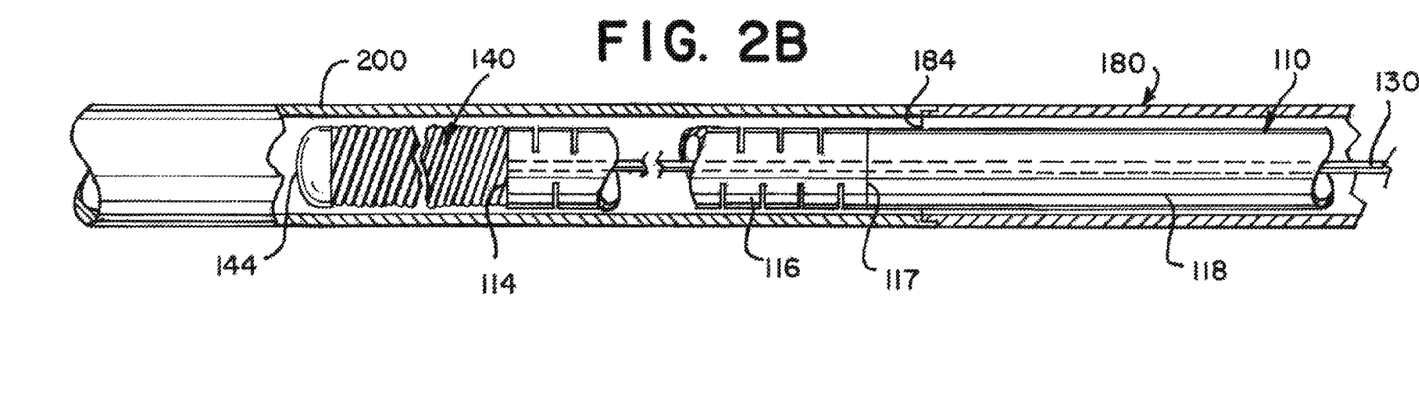

FIGS. 2A and 2B are illustrations of an exemplary implantation system such as illustrated in FIG. 1 interfacing with a microcatheter 200. FIG. 2A illustrates an instant of a treatment procedure near the beginning of the treatment procedure in which an introducer sheath 180 is positioned to cover an embolic implant 140 and a soft portion 116 of a delivery tube 110 in a packaged configuration and a distal end 184 of the introducer sheath 180 is mated or engaged with a proximal end of the microcatheter 200. As shown in FIG. 2A, the distal end 184 of the introducer sheath 180 can be sized to engage the microcatheter 200 to create an enclosed interface through which the embolic implant 140 and the soft portion 116 of the delivery tube 110 can pass. The embolic implant 140 and the delivery tube 110 can be translated distally to push the embolic implant 140 and a portion of the delivery tube 110 into the microcatheter 200.

FIG. 2B illustrates an instant of the treatment procedure in which the embolic implant 140 and the soft portion 116 are positioned within the microcatheter 200. At the instant illustrated in FIG. 2B, the embolic implant 140 and the soft portion 116 are protected by the microcatheter 200 and the introducer sheath can now be pulled proximally 180 or left in place as the delivery tube 110 and embolic implant 140 are further translated distally.

Figure 3A:
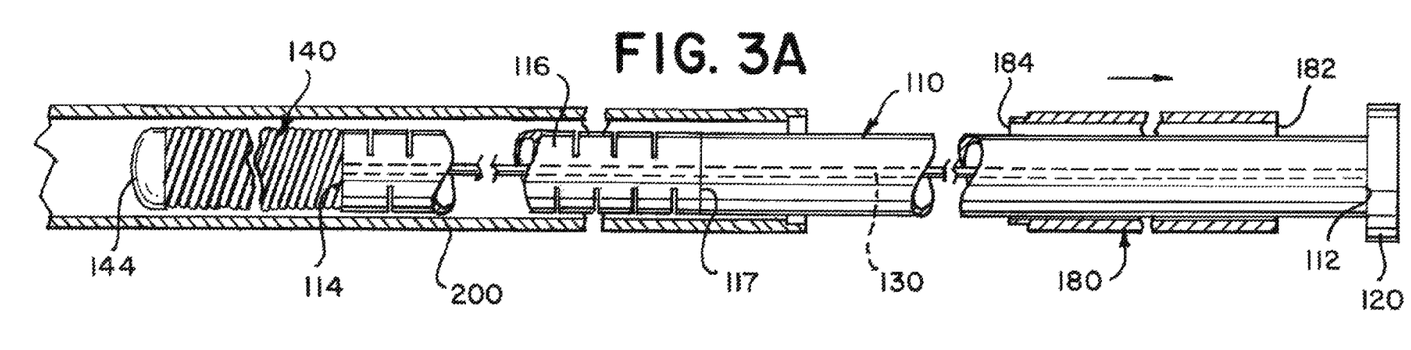
FIGS. 3A through 3C are illustrations of implantation steps that can be performed with an exemplary implantation system such as illustrated in FIG. 1 according to aspects of the present invention.
Figure 3B:
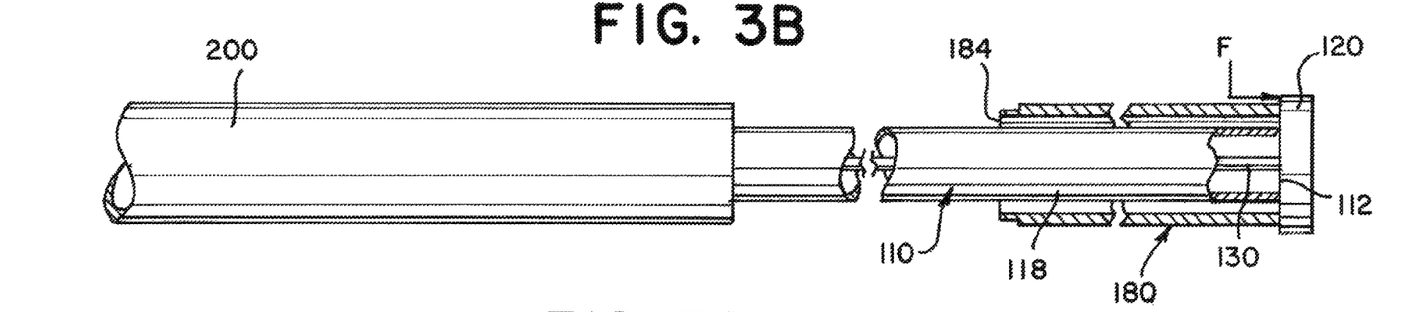
Figure 3C:
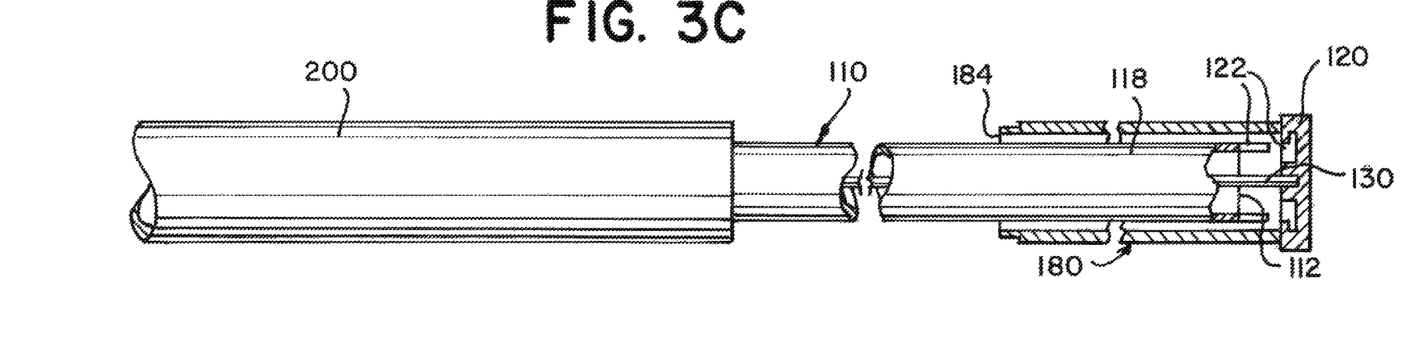

FIGS. 3A through 3C are illustrations of an exemplary implantation system during a series of example implantation steps. FIG. 3A illustrates an embolic implant 140 and a soft portion 116 of a delivery tube 110 positioned inside a microcatheter 200 and an introducer sheath 180 being translated proximally over a proximal portion 118 of the delivery tube 110. As illustrated in FIG. 3A, the introducer sheath 180 can be disengaged from the microcatheter 200 and pulled proximally once the embolic implant 140 and soft section 116 are protected within the microcatheter 200, but before the embolic implant 140 is positioned at a treatment site or within an aneurysm. Alternatively, the introducer sheath 180 can remain engaged to the microcatheter until the embolic implant 140 is positioned at the treatment site or ready to be deployed from the delivery tube 110 and then pulled proximally after the embolic implant 140 is positioned at the treatment site.

FIG. 3B illustrates the introducer sheath 180 in a deployment configuration in which the introducer sheath 180 is engaged with an interference feature 120 positioned near a proximal end 112 of the delivery tube 110. The introducer sheath 180 is shown providing a force F against the interference feature 120. The force can be sufficient to move the interference feature 120 proximally in relation to the delivery tube 110. Prior to the application of the force F, the interference feature 120 can be detachably attached to the proximal end 112 of the delivery tube 110, and the interference feature 120 can be detached from the proximal end 112 of the delivery tube 110 in response to the force F. Alternatively, the interference feature 120 can remain attached to the delivery tube 110 and the force F can be sufficient to move the interference feature 120 in relation to the delivery tube 110.

The introducer sheath 180 can be sized to engage the interference feature 120. As illustrated, the introducer sheath 180 can be tubular and can have a circular proximal end 182, and the interference feature 120 can protrude radially beyond a circumference of the delivery tube 110. The interference feature 120 can be circular, having a circumference larger than a circumference of the proximal end 182 of the introducer sheath 180. The interference feature 120 can provide a flat surface against which the proximal end 182 of the introducer sheath 180 can press. Additionally, or alternatively, the interference feature can have a non-flat surface that can have a slope or a groove for receiving the introducer sheath 180. The interference feature 120 can be a bump positioned near the distal end of the delivery tube that extends beyond the circumference of the delivery tube and extends so that the introducer sheath 180, when slid proximally over the delivery tube 110, must engage the interference feature 120 before sliding completely over and off the proximal end 112 of the delivery tube 110.

FIG. 3C illustrates the interference feature 120 after being moved proximally in relation to the delivery tube 110 in response to the force F from the introducer sheath 180. The interference feature 120 can be attached to a pull wire 130, and the pull wire 130 can be pulled proximally when the interference feature 180 is moved proximally. The interference feature 120 can be detachably attached to the delivery tube 110 prior to the proximal movement of the interference feature 120, and a detachment feature 122 can be manipulated to facilitate the detachment of the interference feature 120. Once detached, the interference feature 120 can be pulled proximally away from the delivery tube 110, and the pull wire 130 can be moved to exit the proximal end 112 of the delivery tube 110 in response to the pulling of the interference feature 120. The pull wire 130 can be an elongated member that extends through a lumen of the delivery tube 110 toward the embolic implant 140. The pull wire 130 can constitute a component of a deployment system for releasing the embolic implant 140 at the distal end 114 of the delivery tube 110. When the pull wire 130 is pulled proximally, the pull wire 130 can initiate the deployment of the embolic implant 140. The embolic implant 140 can be detached from the delivery tube 110 in response to the proximal movement of the pull wire 130 in relation to the delivery tube 110.

Figures 4A, 4B, 5B:
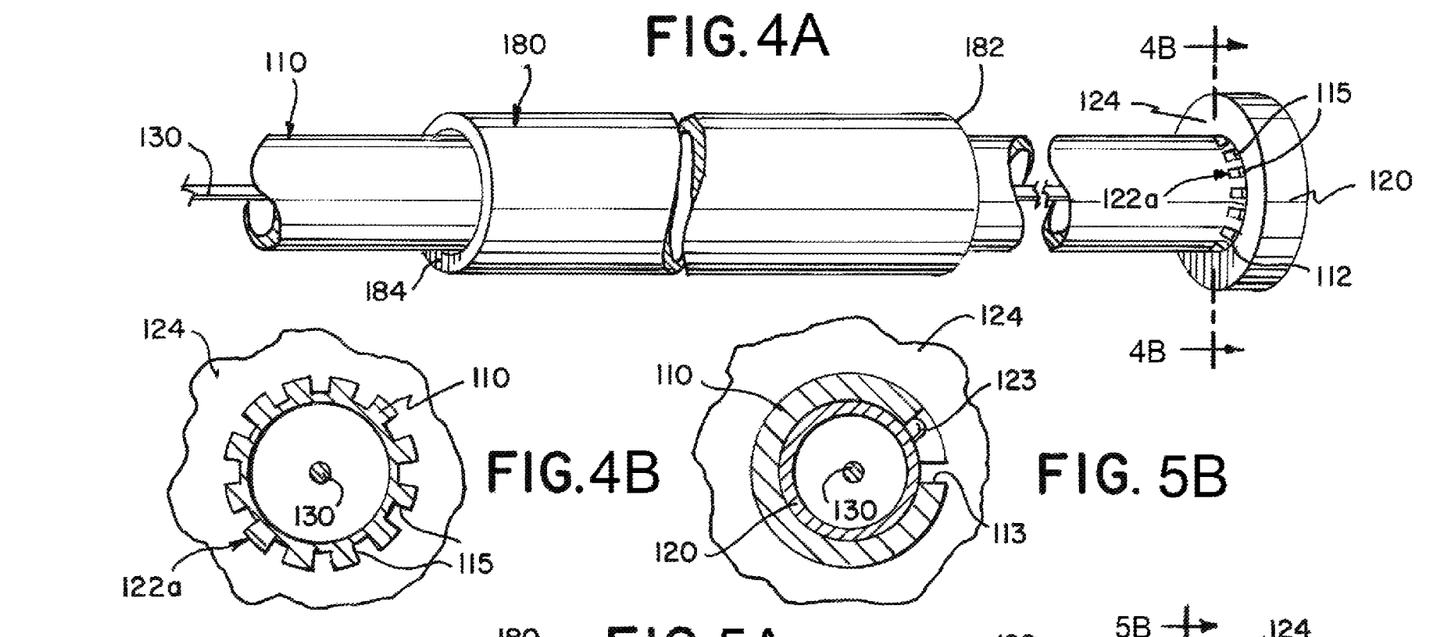
FIG. 4A illustrates an exemplary implantation system having a breakable disconnection feature according to aspects of the present invention.
FIG. 4B illustrates a cross-sectional view near a proximal end of the exemplary implantation system of FIG. 4A as indicated in FIG. 4A and according to aspects of the present invention.
FIG. 5B illustrates a cross-sectional view near a proximal end of the exemplary implantation system of FIG. 5A as indicated in FIG. 5A and according to aspects of the present invention.

FIG. 4A illustrates an exemplary implantation system having a breakable disconnection feature 122a. The implantation system can have an interference feature 120 detachably attached to a delivery tube 110 by the breakable disconnection feature 122a. The delivery tube 110 can include notches 115 that are areas in which material is removed from the delivery tube 110. The notches 115 can be positioned at a proximal end 112 of the delivery tube 110. The proximal end 112 of the delivery tube 110 can be attached to the interference feature 120 by gluing, welding, or other means. The notches 115 can be a breakable section 122a of the delivery tube 110. When an introducer sheath 180 is pressed against the interference feature 120, a force from the interference feature 120 can cause the breakable section 122a to break, and the interference feature 120 can then be moved proximally in relation to the delivery tube 110. The interference feature 120 can have a circular surface 124 against which the introducer sheath 180 can press. FIG. 4B is a cross-sectional view near a proximal end of the exemplary implantation system as indicated in FIG. 4A.

Figure 5A:
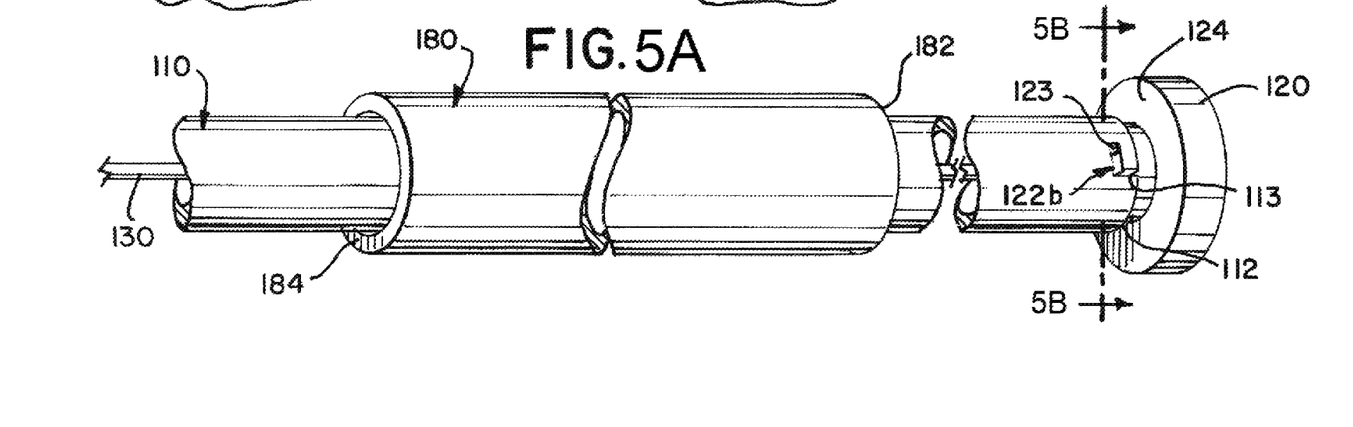
FIG. 5A illustrates an exemplary implantation system having a twist-lock disconnection feature according to aspects of the present invention.

FIG. 5A illustrates an exemplary implantation system having a twist-lock disconnection feature 122b. The implantation system can have a delivery tube 110 with groove 113 cut at a proximal end 112 and an interference feature 120 that has a bump 123 or another feature that can engage the groove 113. The interference feature 120 can be detachably attached to the delivery tube 110 by the twist-lock disconnection feature (and/or a bayonet connector) 122b. The interference feature 120 can extend within a lumen of the delivery tube 110 at the proximal end 112 of the delivery tube 110 and have a bump or protrusion 123 that can be positioned in the groove 113 in the delivery tube 110 to maintain the attachment between the interference feature 120 and the delivery tube 110. The bump or protrusion 123 can be slid through the groove 113 to detach the interference feature 120 from the delivery tube 110. The groove 113 can be L shaped, and the interference feature 120 can be twisted in relation to the delivery tube 110 and then pulled proximally in relation to the delivery tube 110 to disconnect the twist-lock disconnection feature 122b. FIG. 5B illustrates a cross-sectional view near a proximal end of the exemplary implantation system as indicated in FIG. 5A.

While FIGS. 4A through 5B illustrate examples of an interference feature 120 that is movable in relation to the delivery tube 110 after detaching from the delivery tube 110, the interference feature need not be detached, and can be movable in relation to the delivery tube 110 without detaching. FIGS. 6A through 8C illustrate example systems wherein the interference feature 120 remains at least partially attached to the delivery tube 110.

Figure 6A:
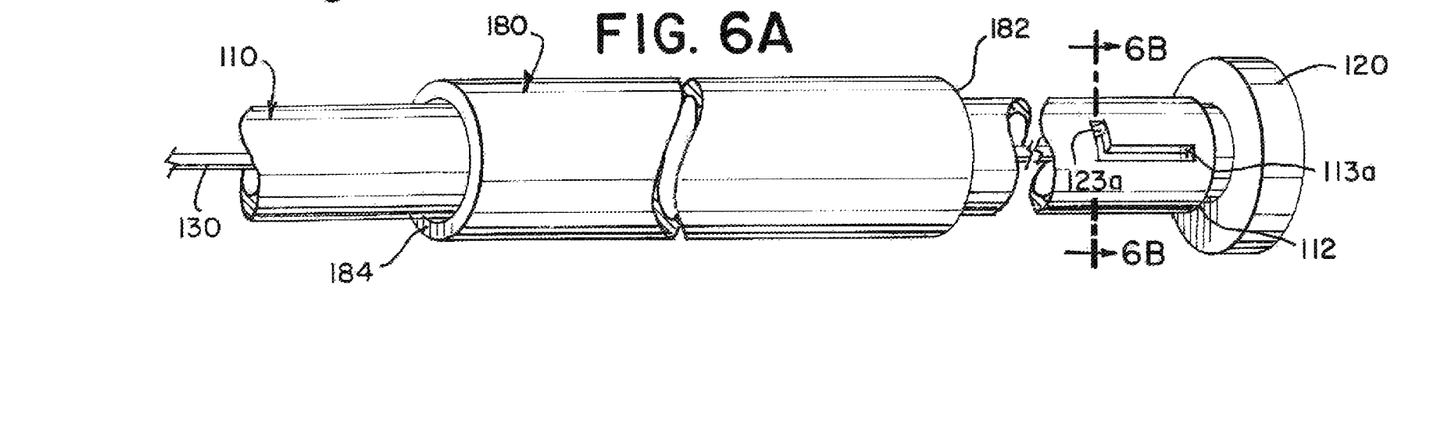
FIG. 6A illustrates an exemplary implantation system having a sliding track according to aspects of the present invention.
Figures 6B, 7A, 7B:
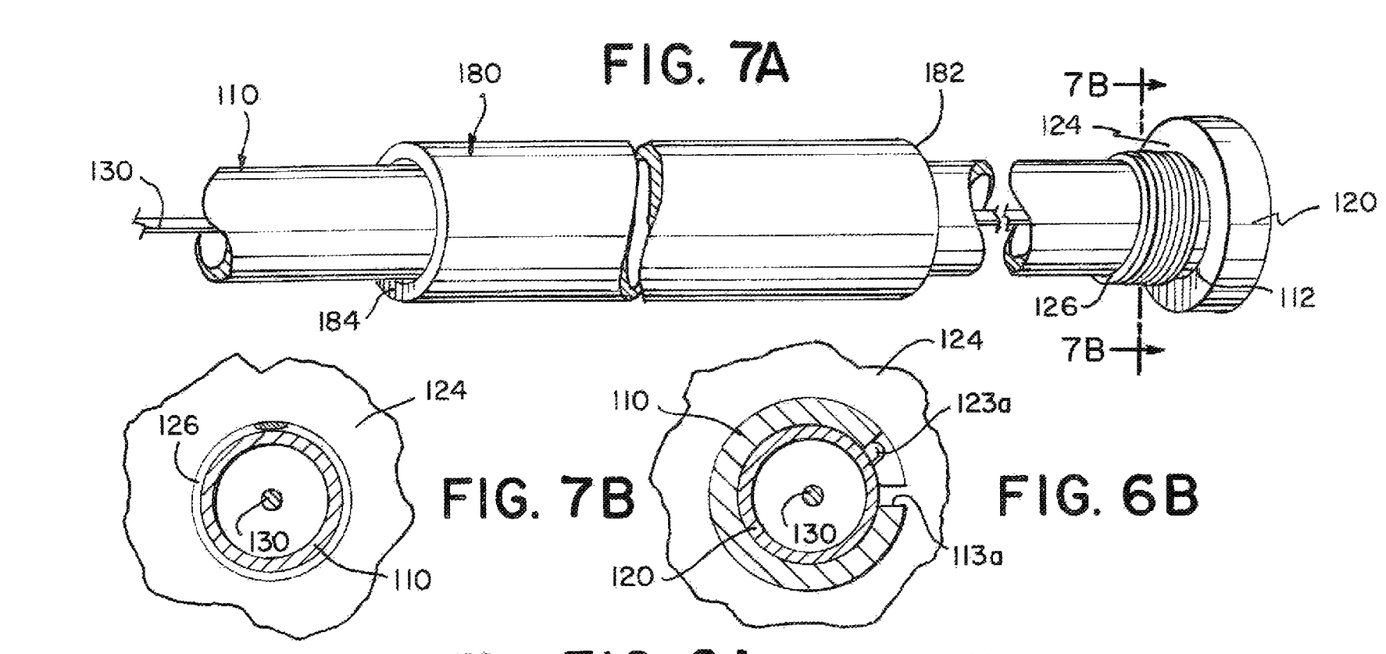
FIG. 6B illustrates a cross-sectional view near a proximal end of the exemplary implantation system of FIG. 6A as indicated in FIG. 6A and according to aspects of the present invention.
FIG. 7A illustrates an exemplary implantation system having a stretchable segment according to aspects of the present invention.
FIG. 7B illustrates a cross-sectional view near a proximal end of the exemplary implantation system of FIG. 7A as indicated in FIG. 7A and according to aspects of the present invention.

FIG. 6A illustrates an exemplary implantation system having a sliding track 113a and a bump or protrusion 123a. The sliding track 113a can be cut from a portion of the delivery tube 110 near the proximal end 112 of the delivery tube 110. The interference feature 120 can have an engagement bump or protrusion 123a that is positioned to slide within the track 113a. The track 113a can extend along a portion of a length of the delivery tube 110, and the bump 123a can slide within the track 113a, allowing the interference feature 120 to move in a proximal direction in relation to the delivery tube 110. The track 113a can be L shaped, and the interference feature 120 can be twisted in relation to the delivery tube 110 and then pulled proximally in relation to the delivery tube 110 to move the interference feature 120 in relation to the delivery tube 110. The interference feature 120 can be attached to a pull wire 130, and the movement of the interference feature 120 can move the pull wire 130 to deploy an embolic implant 140. FIG. 6B illustrates a cross-sectional view near a proximal end of the exemplary implantation system as indicated in FIG. 6A.

FIG. 7A illustrates an exemplary implantation system having a stretchable segment 126. The implantation system can have a delivery tube 110 with a stretchable segment 126 positioned near a proximal end 112 of the delivery tube 110. The stretchable segment 126 can be a region of the delivery tube 110 that has a propensity to stretch in response to a force that creates tension along a length of the delivery tube 110 that includes the stretchable segment 126. The stretchable segment 126 can include a coil that is compressed in an initial state as illustrated in FIG. 7A, a laser cut portion of the tube, and/or a portion of tubing having greater elasticity. The stretchable segment 126 can extends in response to a force provided by the introducer sheath 180 against the interference feature 120. The stretchable segment 126 can allow the pull wire and the interference feature 120 to move proximally in relation to the delivery tube 110 without the interference feature 120 becoming disconnected from the delivery tube 110. The stretchable segment 126 can have a fully extended length that is determined by the material properties and/or construction of the stretchable segment 126. The fully extended length can limit the distance that the interference feature 120 can be moved proximally in relation to the delivery tube 110. FIG. 7B illustrates a cross-sectional view near a proximal end of the exemplary implantation system as indicated in FIG. 7A.

Figure 8A:
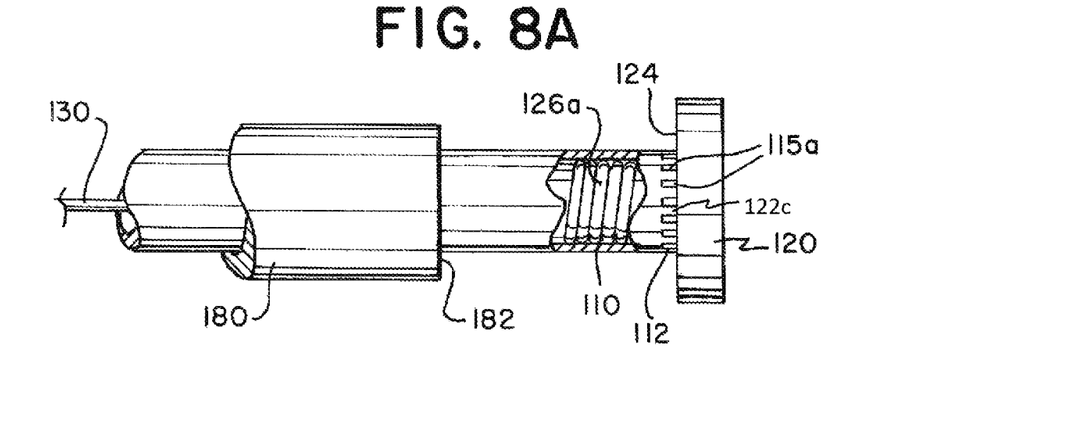
FIGS. 8A through 8C illustrate cut-away views of an exemplary implantation system having a stretchable segment and a disconnecting feature according to aspects of the present invention.
Figure 8B:
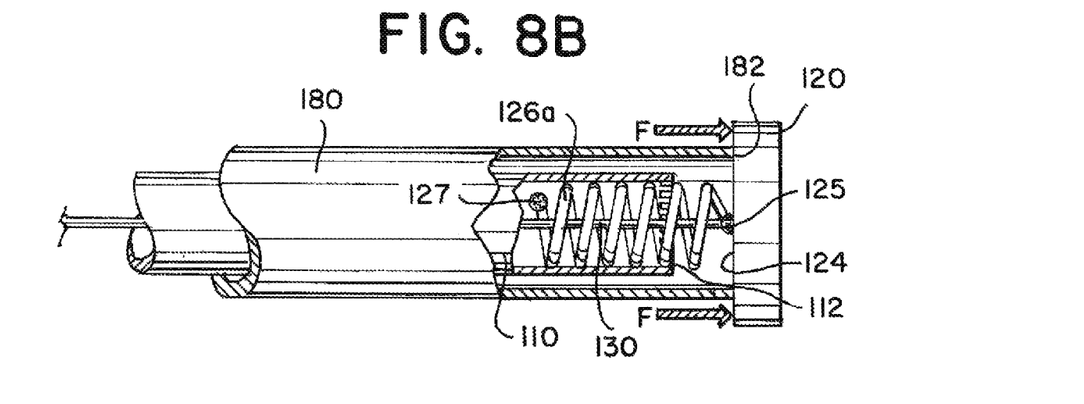
Figure 8C:
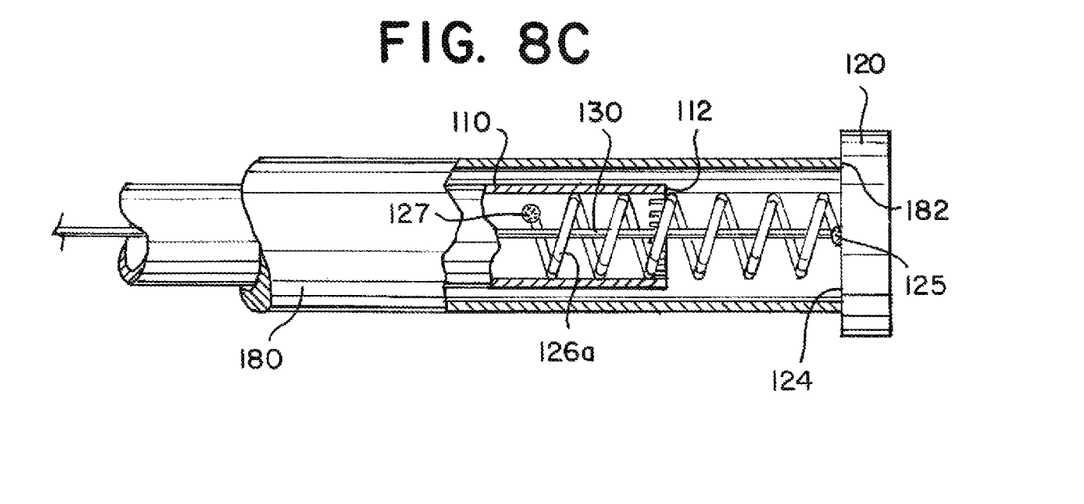

FIGS. 8A through 8C illustrate an exemplary implantation system having a stretchable element 126a and a detachment feature 122c. The disconnection feature 122c illustrated in FIGS. 8A through 8C can include notches 115B in a delivery tube 110, similar to that illustrated in FIGS. 4 and 4B. It is contemplated that other disconnection features, including the disconnection features illustrated in, and described in relation to FIGS. 1, 3A-3C, 5, or 5B could be combined with a stretchable segment like those described herein or otherwise known. When used in combination with the stretchable segment 126a, the disconnection feature 122c can be positioned along a length of the delivery tube 110 at or near the stretchable segment 126a. Both the stretchable segment 126a and the disconnection feature 122c can be positioned near the proximal end 112 of the delivery tube 110.

FIG. 8A illustrates the stretchable element 126a positioned within a lumen of the delivery tube 110 near the proximal end 112 of the delivery tube 110. In FIG. 8A, the delivery tube 110 is illustrated cut-away to show coils of the stretchable element 126a within. In the configuration illustrated in FIG. 8A, interference feature 120 can be attached to the delivery tube 110 via the stretchable element 126a and the detachment feature 122c.

FIG. 8B illustrates an introducer sheath 180 moved proximally to engage the interference feature 120, break the detachment feature 122c, and begin to stretch the stretchable element 126a. The delivery tube 110 and the introducer sheath 180 are shown cut-away. A pull wire 130 can be positioned within the delivery tube 110. The pull wire 130 can be pulled proximally as the interference feature 120 is moved proximally. The stretchable element 126a can be attached to the interference feature 120 with a weld, adhesive, or other connection 125. The stretchable element 126a can be attached to the delivery tube 110 with a weld, adhesive, or other connection 127. After the detachment feature 122c is detached, the stretchable element 126a can maintain an attachment between the interference feature 120 and the delivery tube 110.

FIG. 8C illustrates the introducer sheath 180 moved further proximally to move the interference feature 120 and pull wire 130 further proximally and further stretch the stretchable element 126a. The stretchable element 126a can have a fully extended length that is determined by the material properties and/or construction of the stretchable element 126a. The fully extended length can limit the distance that the interference feature 120 can be moved proximally in relation to the delivery tube 110.

Figure 9:
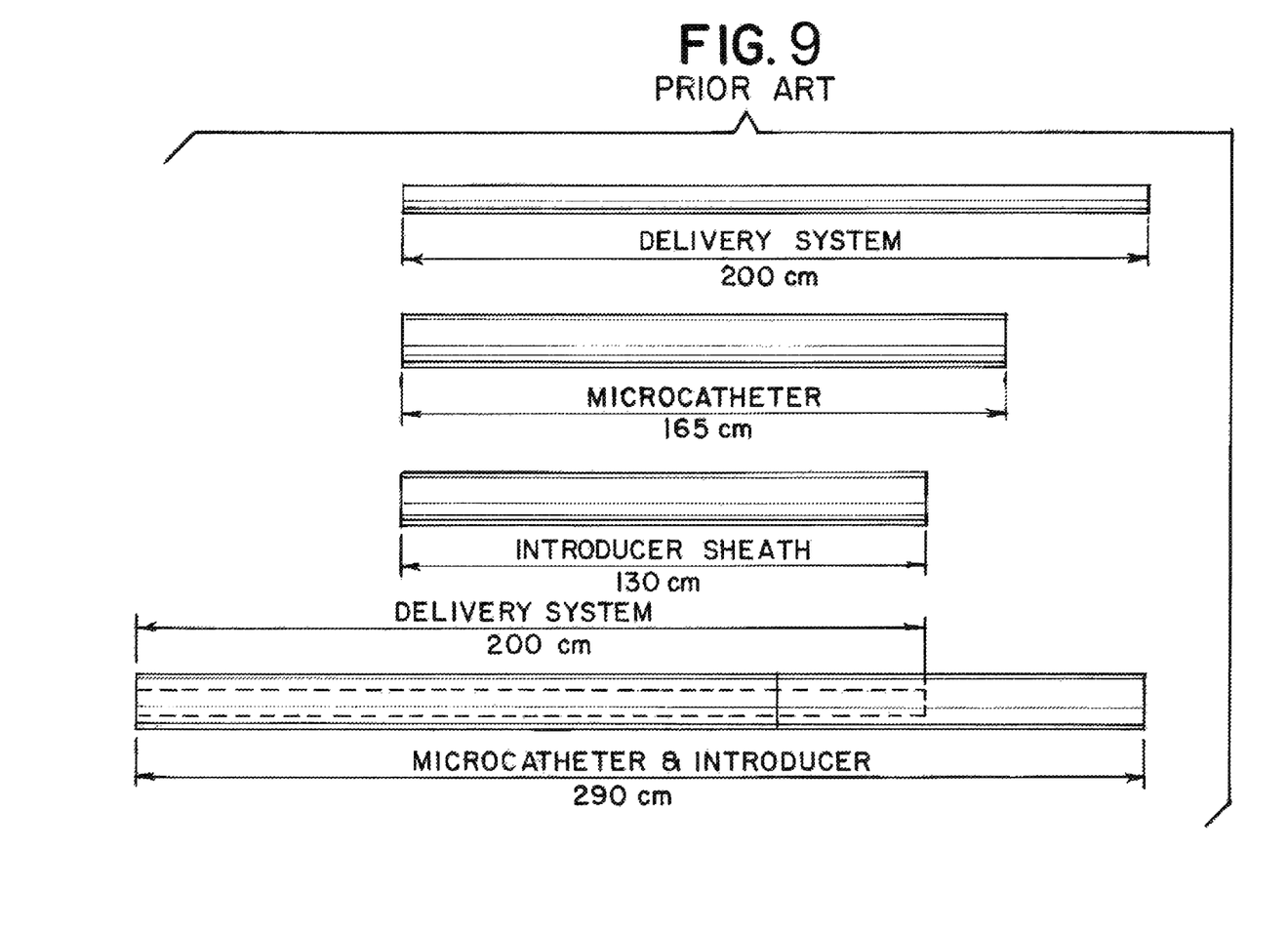
FIG. 9 illustrates relative dimensions of a delivery system, microcatheter, and introducer sheath as known in the art.

FIG. 9 illustrates relative dimensions of a delivery system, microcatheter, and introducer sheath as known in the art. Known delivery systems are typically 200 cm long, known microcatheters are typically 165 cm long, and known introducer sheaths are typically 130 cm long. In known practices, the introducer sheath is typically removed after an embolic implant and any sensitive portions of the delivery system are inserted into the microcatheter. According to known practices, an introducer sheath cannot remain around the delivery system during the deployment step of the embolic implant because the combined length of known microcatheters and introducers is several centimeters longer than known delivery systems. It is an aspect of the present invention to size a delivery system and an introducer sheath so that the introducer sheath can remain on the delivery system through the embolic implant deployment step. In example systems presented herein, an implantation system can include a delivery system, microcatheter, and introducer sheath, wherein the delivery system is longer than the combined length of the microcatheter and the introducer sheath.

An aneurysm can be treated with an implantation system such as any of the implantation systems disclosed herein in relation to the present invention by executing some or all the following steps, not necessarily in order. An implantation system 100 having an embolic implant 140, an introducer sheath 180, a delivery tube 110, an interference feature 120, and a pull wire 130 can be provided. The pull wire 130 can be affixed to the interference feature 120. The pull wire 130 can be positioned within a lumen of the delivery tube 110. The interference feature 120 can be attached to a proximal end 112 of the delivery tube 110. The embolic implant 140 can be attached at a distal end 114 of the delivery tube 110. The introducer sheath 180 can be positioned to encompass the embolic implant 140 and a first portion of the delivery tube 110. The first portion of the delivery tube 110 can comprise a soft section 116. The introducer sheath can be sized to have an end-to-end length that is longer by about 5 cm than a length measurable from a distal end 144 of the embolic implant 140 to a proximal end 117 of the soft section 116. The introducer sheath 180 can be sized so that the end-to-end length is between about 46 cm and about 105 cm. A microcatheter 200 can be provided. The introducer sheath 180 can be positioned to engage with the microcatheter 200 while maintaining the embolic implant 140 and the first portion of the delivery tube 110 within the introducer sheath 180. The embolic implant 140 and the delivery tube 110 can be translated distally to position the embolic implant 140 and the first portion of the delivery tube 110 within the microcatheter 200. The introducer sheath 180 can be slid proximally over the delivery tube 110. The introducer sheath 180 can be pulled proximally to apply a force from the introducer sheath 180 to the interference feature 120. The interference feature 120 and the pull wire 130 can be moved proximally in relation to the delivery tube 110 in response to the force. The interference feature 120 can be detached from the delivery tube 110. The embolic implant 140 can be detached from the delivery tube 110 in response to moving the interference feature 120 and the pull wire 130 proximally in relation to the delivery tube 110.

The descriptions contained herein are examples of embodiments of the invention and are not intended in any way to limit the scope of the invention. As described herein, the invention contemplates many variations and modifications of the implantation system and associated methods, including alternative geometries of system components, alternative materials, additional or alternative method steps, etc. These modifications would be apparent to those having ordinary skill in the art to which this invention relates and are intended to be within the scope of the claims which follow.

The invention claimed is:

1. An implantation system comprising:
   a delivery tube comprising a lumen therethrough, a proximal end, and a distal end;

an embolic coil detachably attached to the distal end of the delivery tube;
an introducer sheath comprising a lumen therethrough sized to slidably receive the delivery tube and the embolic coil;
an interference feature positioned approximate the proximal end of the delivery tube; and
an elongated member disposed within the lumen of the delivery tube and attached to the interference feature, wherein the introducer sheath is translatable over the delivery tube from the distal end of the delivery tube to the proximal end of the delivery tube and is sized to engage the interference feature,
wherein the interference feature is movable in relation to the delivery tube in response to a force applied by the introducer sheath against the interference feature, and
wherein the elongated member is movable in relation to the delivery tube in response to a proximal movement of the interference feature.

2. The system of claim 1 wherein the interference feature is detachable from the delivery tube and wherein the elongated member is movable to exit the proximal end of the delivery tube in response to a proximal movement of the detached interference feature.

3. The system of claim 1
wherein the delivery tube comprises a soft section disposed approximate the distal end of the delivery tube,
wherein a first length is measurable from a distal end of the embolic coil to a proximal end of the soft section, and
wherein the introducer sheath comprises a second length measurable from a distal end to a proximal end of the introducer sheath, the second length measuring greater than the first length by about 5 cm.

4. The system of claim 3 further comprising a microcatheter comprising a third length measurable from a distal end to a proximal end of the microcatheter, and wherein the delivery tube comprises a fourth length measurable from the distal end to the proximal end of the delivery tube, the fourth length measuring greater than the sum of the third length and the second length.

5. The system of claim 1 wherein the introducer sheath comprises a length of between about 46 cm to about 105 cm, the length measurable from a distal end to a proximal end of the introducer sheath.

6. The system of claim 1
wherein the delivery tube comprises a soft section disposed approximate the distal end of the delivery tube, and
wherein the introducer sheath is movable from a packaged configuration in which the introducer sheath is positioned to completely encompass the soft section and the embolic coil to a deployment configuration in which the introducer sheath is engaged with the interference feature.

7. The system of claim 1 wherein the embolic coil is detachable from the delivery tube in response to a proximal movement of the elongated member in relation to the delivery tube.

8. The system of claim 1 wherein the interference feature comprises a substantially circular surface positioned to engage the proximal end of the introducer sheath.

9. An implantation assembly comprising:
a delivery tube comprising a lumen therethrough, a proximal end, and a distal end;
an embolic implant attached to the distal end of the delivery tube;
a pull wire disposed within the lumen of the delivery tube and movable to detach the embolic implant from the delivery tube;
an engagement bump disposed on a proximal end of the pull wire and positioned approximate the proximal end of the delivery tube; and
a tubular sheath conveyable over the embolic implant and the delivery tube from a distal end of the embolic implant to the proximal end of the delivery tube, the tubular sheath sized to engage the engagement bump, wherein the engagement bump and the pull wire are movable in relation to the delivery tube in response to a force applied by the tubular sheath to the engagement bump.

10. The assembly of claim 9
wherein the delivery tube comprises a soft section extending proximally from the distal end of the delivery tube,
wherein a first length is measurable from the distal end of the embolic implant to a proximal end of the soft section, and
wherein the tubular sheath comprises a second length measurable from a distal end to a proximal end of the tubular sheath, the second length measuring greater than the first length by about 5 cm.

11. The assembly of claim 10 further comprising a microcatheter comprising a third length measurable from a distal end to a proximal end of the microcatheter, and wherein the delivery tube comprises a fourth length measurable from the distal end of the delivery tube to the proximal end of the delivery tube, the fourth length measuring greater than the sum of the third length and the second length.

12. The assembly of claim 9
wherein the delivery tube comprises a soft section extending proximally from the distal end of the delivery tube, and
wherein the tubular sheath is movable from a packaged configuration in which the tubular sheath is positioned to completely encompass the soft section and the embolic implant to a deployment configuration in which the tubular sheath is engaged with the engagement bump.

13. The assembly of claim 9 wherein the engagement bump is detachable from the delivery tube in response to the force applied by the tubular sheath.

14. The assembly of claim 9 wherein pull wire is movable to detach the embolic implant from the delivery tube in response to the force applied by the tubular sheath.

15. A method for treating an aneurysm comprising:
providing an implantation system comprising an embolic implant, an introducer sheath, a delivery tube, an interference feature, and a pull wire;
affixing the pull wire to the interference feature;
positioning the pull wire within a lumen of the delivery tube;
attaching the interference feature to a proximal end of the delivery tube;
attaching the embolic implant at a distal end of the delivery tube;
positioning the introducer sheath to encompass the embolic implant and a first portion of the delivery tube;
sliding the introducer sheath proximally over the delivery tube;
pulling the introducer sheath proximally to apply a force from the introducer sheath to the interference feature; and moving the interference feature and the pull wire proximally in relation to the delivery tube in response to the force.

16. The method of claim 15
wherein the first portion of the delivery tube comprises a soft section, and
wherein a first length is measurable from a distal end of the embolic implant to a proximal end of the soft section,
the method further comprising sizing the introducer sheath to comprise a second length measurable from a distal end to a proximal end of the introducer sheath, the second length measuring greater than the first length by about 5 cm.

17. The method of claim 15 further comprising sizing the introducer sheath to comprise a length of between about 46 cm to about 105 cm, the length measurable from a distal end to a proximal end of the introducer sheath.

18. The method of claim 15 further comprising detaching the embolic implant from the delivery tube in response to moving the interference feature and the pull wire proximally in relation to the delivery tube.

19. The method of claim 15 further comprising detaching the interference feature from the delivery tube.

20. The method of claim 15 further comprising:

providing a microcatheter;

positioning the introducer sheath to engage with the microcatheter while maintaining the embolic implant and the first portion of the delivery tube within the introducer sheath; and translating the embolic implant and the delivery tube distally to position the embolic implant and the first portion of the delivery tube within the microcatheter.

* * * * *